US00PP37747P3

(12) United States Plant Patent
Bull

(10) Patent No.: US PP37,747 P3
(45) Date of Patent: Oct. 6, 2026

(54) ***HELIOPSIS* PLANT NAMED 'BullHeliopsisscabra 01'**

(50) Latin Name: ***Heliopsis helianthoides* var. *scabra***
Varietal Denomination: BullHeliopsisscabra 01

(71) Applicant: Hartwig Bull, Gönnebek (DE)

(72) Inventor: Hartwig Bull, Gönnebek (DE)

( * ) Notice: Subject to any disclaimer, the term of this patent is extended or adjusted under 35 U.S.C. 154(b) by 0 days.

(21) Appl. No.: 19/235,276

(22) Filed: Jun. 11, 2025

(65) Prior Publication Data

US 2025/0386754 P1 Dec. 18, 2025

Related U.S. Application Data

(60) Provisional application No. 63/731,836, filed on Jun. 12, 2024.

(51) Int. Cl.
*A01H 5/02* (2018.01)
*A01H 6/14* (2018.01)

(52) U.S. Cl.
USPC ..... Plt./437
CPC ..... *A01H 6/14* (2018.05); *A01H 5/02* (2013.01)

(58) Field of Classification Search
USPC ..... Plt./437
CPC ..... A01H 5/02; A01H 5/00; A01H 6/14
See application file for complete search history.

(56) References Cited

PUBLICATIONS

Missouri Plants *Heliopsis helianthoides* (L.) Sweet Ox-Eye, retrieved on Sep. 9, 2025 at https://www.missouriplants.com/Heliopsis_helianthoides_page.html, 7 pp. (Year: 2025).*

* cited by examiner

*Primary Examiner* — June Hwu
(74) *Attorney, Agent, or Firm* — The Webb Law Firm

(57) ABSTRACT

A new and distinct variety of *Heliopsis* plant having a compact growth habit and yellow-orange blooms.

1 Drawing Sheet

Botanical classification: *Heliopsis helianthoides* var. *scabra.*

Varietal denomination: 'BullHeliopsisscabra 01'.

BACKGROUND OF THE INVENTION

The present invention relates to a new and distinct cultivar of *Heliopsis* plant, known by the varietal name 'BullHeliopsisscabra 01'. The new variety was discovered in August of 2020 in Gönnebek, Germany as the result of a planned breeding program with the purposes of providing compact *Heliopsis* plants with different flower colors, good growth habit, improved uniformity, good branching, good propagation rates, and that perform well. The new variety is the result of a cross between an unpatented *Heliopsis* variety having an internal breeder's reference of "BulHs 2018-03" (female parent) and an unpatented *Heliopsis* variety having an internal breeder's reference of "BulHs-2018-11" (male parent) from the breeder's own collection. The new variety was first asexually reproduced via in-vitro tissue culture cuttings in Gönnebek, Germany in September of 2020. The new variety is similar to its parental varieties in botanical classification, but exhibits more compactness, a greater number of flowers, specifically yellow-orange flowers, with good self-branching, more branches, and dark-green small leaves than the parental varieties.

When 'BullHeliopsisscabra 01' is compared to *Heliopsis* variety named 'Hohlspiegel' (unpatented), 'BullHeliopsisscabra 01' is similar to 'Hohlspiegel' in botanical classification and the presence of orange-yellow flowers, but 'BullHeliopsisscabra 01' exhibits greater compactness, a greater branching habit that is very even, a greater number of flowers, including pure orange flowers, and nicer, cleaner leaves having a green color, no necroses in the leaves or at the edges of the leaves, no brown spots in the middle of the leaves, that distinguish it from 'Hohlspiegel'. Further, the following characteristics distinguish 'BullHeliopsisscabra 01' when generally compared to other *Heliopsis* varieties known to the breeder:

Much more compact;
Good self-branching habit;
A great number of yellow-orange flowers;
Small leaves;
Very uniform growth;
Nice dark green leaves;
Fast crop time;
Long-lasting flowers; and
Good hardiness as a perennial.

The new variety has been trial and field tested and has been found to retain its distinctive characteristics and remain true to type through successive asexual propagations. The present invention has not been evaluated under all possible environmental conditions. The phenotype may vary with variations in environment without a change in the genotype of the plant.

DESCRIPTION OF THE DRAWINGS

The accompanying photographic drawings illustrate the new variety at 20 weeks of age, with the color being as nearly true as is possible with color illustrations of this type:

FIG. 1 shows an entire plant of the new variety.

DESCRIPTION OF THE PLANT

The following detailed description sets forth the characteristics of the new variety as the result of asexual reproductions performed via in vitro tissue culture cuttings carried out in Gönnebek, Germany. Plants of the new variety were grown outdoors in 15 cm (1.5 liter) pots under normal field production conditions (2 pinches), and the color readings and measurements were observed outdoors under natural light on 20-week-old plants in Gönnebek, Germany. Color references are primarily to The 2015 R.H.S. Colour Chart of The Royal Horticultural Society of London, Sixth Edition, except where terms of ordinary significance are used.

PLANT

Time to initiate roots: About 10 days at about 19-20° C.
Time to develop roots: About 40 days at about 18° C.
Time to produce a finished flowering plant from a rooted cutting: About 10-12 weeks in a 15 cm container.
Rooting habit and description: Lots of roots, free branching nice healthy-looking root system.
Plant height: 30.0-40.0 cm.
Plant width: 25.0-30.0 cm.
Vigor: Approximately 4-5 weeks to root from a cutting, with another three weeks (with a single pinch) to develop a finished young plant. The time from a finished young plant to a finished plant, with another pinch, is approximately 10-12 weeks.
Branching habit: Lot of branches, upright, shows a medium compact plant.
Lateral branches:
*Number per plant.*—15-20.
*Length.*—15.0-35.0 cm.
*Diameter.*—3.0-6.0 mm.
*Internode length.*—1.0-5.0 cm.
*Angle.*—Upright, outward.
*Strength.*—Strong.
*Texture.*—Pubescent.
*Color.*—Gray-brown (close to N199A).
Foliage:
*Arrangement.*—Single.
*Leaf.*—Acuminate. Length: 2.5-10.0 cm. Width: 1.0-5.0 cm. Shape: Acuminate. Apex: Acute. Base: Rounded to Acute. Texture: Upper surface: Rough. Lower surface: Rough. Aspect: Straight to curved. Margin: Serrate. Color: Young leaves: Upper surface: Green (close to NN137B). Lower surface: Green (close to 138B). Mature leaves: Upper surface: Green (close to NN137B). Lower surface: Green (close to 138 B). Petiole: none. Length: 1-3 cm. Diameter: 2-3 mm. Texture: Strong. Color: Gray-brown (close to N199A). Veins: Venation type: cross venulate. Color: Upper surface: Gray-brown (N199A) to green (close to N138B). Lower surface: Gray Brown (N199A) to green (close to N138B).

INFLORESCENCE

Bud:
*Appearance.*—Elliptic sharped ray florets and tubular disk floret.
*Diameter.*—1.5-3.0 cm.
*Length.*—1.0-1.6 cm.
*Color.*—Green (close to 147C).
*Natural flowering season.*—July-September in Gönnebek, Germany, beginning approximately 10-12 weeks after planting.
Inflorescence form and disc/ray arrangement description: Single flower.
Average number of inflorescences per plant: 20-30.
Disc and ray floret arrangement: Single composite flower.
Number of inflorescences per branch: 1-3.
Fragrance: None.
Peduncle: Single, with a length of about 1.5-6.0 cm and having a rough surface. Color is NN137A up to N199A.
Inflorescence:
*Diameter.*—4.0-10.0 cm.
*Height (depth).*—2.0-4.5 cm.
*Diameter of disc.*—1.5-4.0 cm.
*Receptacle height.*—1.0 cm.
*Receptacle diameter.*—1.5-4.0 cm.
Ray florets:
*Number per inflorescence.*—16-24.
*Arrangement.*—In two or three whorls.
*Length.*—1.5-3.5 cm.
*Width.*—0.9-1.5 cm.
*Shape.*—Elliptical.
*Apex.*—Notched as shallow (approximately 1-2 mm).
*Base.*—Acute.
*Margin.*—Entire.
*Texture.*—Upper surface: Smooth, glabrous. Lower surface: Rough.
*Color.*—When opening: Upper surface: Orange (close to 21A). Lower surface: Orange (close to 35A). At maturity: Upper surface: Orange (close to 21A). Lower surface: Orange (close to 35A). Ground color description: Orange.
*Venation.*—Appearance: Color: Upper surface: Same color as florets. Lower surface: Same color as florets.
Disc florets:
*Number per inflorescence.*—Numerous disk florets.
*Arrangement.*—In center of receptacle.
*Length.*—8.0-15.0 mm.
*Width.*—1.0-2.0 mm.
*Shape.*—Tubular.
*Apex.*—Divided and five-pointed.
*Color.*—Immature: Orange (close up to 23A). At maturity: Orange (close up to 23A).
Phyllaries:
*Number per inflorescence.*—12-18.
*Arrangement.*—In 2 whorls.
*Length.*—0.3-0.7 cm.
*Width.*—4.0-6.0 mm.
*Shape.*—Ovate.
*Apex.*—Elongate, oval.
*Base.*—Fused.
*Margin.*—Entire.
*Texture.*—Upper surface: Rough. Lower surface: Rough.
*Color.*—Immature: Upper surface: Green (close to N138B). Lower surface: Green (close to N138B). At maturity: Upper surface: Green (close to N138B). Lower surface: Green (close to N138B).

REPRODUCTION ORGANS

Androecium:
*Presence.*—On disk florets.
*Number (per floret).*—One.

*Filament length.*—1.0-2.0 mm.

*Filament color.*—Orange (close to 23A).

*Anther.*—Shape: Oval. Length: 1.0 mm. Color: Orange (close to 23B).

*Pollen.*—Color: Yellow (close to 15B). Amount: Lots of Quantity.

Gynoecium:

*Presence.*—In Disk and Ray florets.

*Pistil length.*—1-2 mm.

*Stigma.*—Shape: Two parted. Color: Brown (close to 165A) when closed and Orange (close to 23A) when open.

*Style.*—Length: 1.0-2.0 mm. Color: orange (close to 23A).

Description of seeds/fruits: 1.0-2.0 mm.

Disease/pest resistance: Not observed to date.

Plant hardiness zone: USDA Hardiness Zone 4-5.

I claim:

1. A new and distinct variety of *Heliopsis* plant named 'BullHeliopsisscabra 01', as is herein illustrated and described.

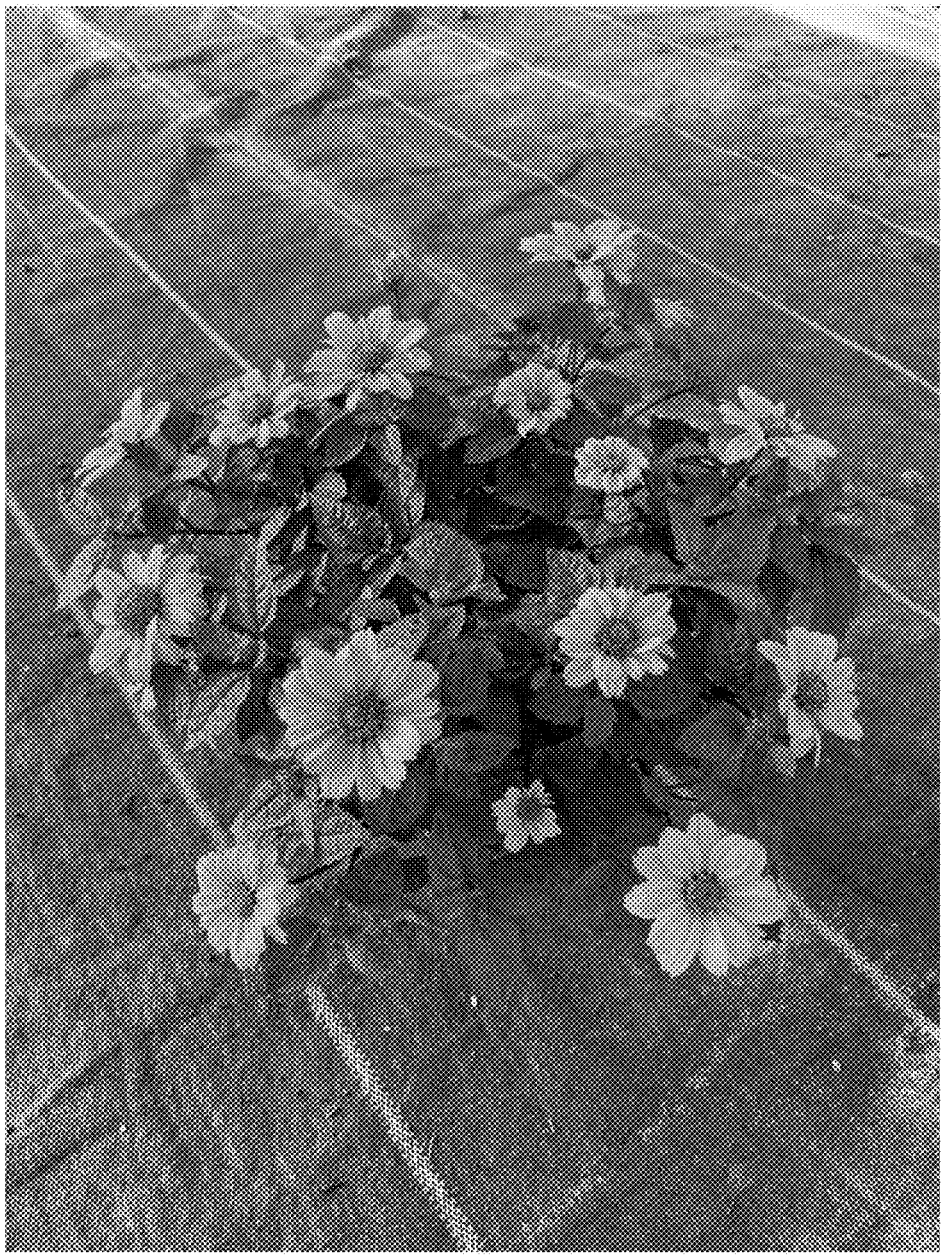

* * * * *